United States Patent [19]

Aschwanden et al.

[11] Patent Number: 4,513,002
[45] Date of Patent: Apr. 23, 1985

[54] CYCLOHEPTENE DERIVATIVES

[75] Inventors: Werner Aschwanden, Ettingen; Quirico Branca, Basel; Emilio Kyburz, Reinach; Rudolf Pfister, Basel, all of Switzerland

[73] Assignee: Hoffmann-La Roche Inc., Nutley, N.J.

[21] Appl. No.: 330,733

[22] Filed: Dec. 14, 1981

[30] Foreign Application Priority Data

Jan. 16, 1981 [CH] Switzerland ............... 273/81

[51] Int. Cl.$^3$ ............................................. A61K 31/40
[52] U.S. Cl. ................................. 514/408; 548/528; 260/456 R; 260/456 P; 570/183
[58] Field of Search ........................ 548/528; 424/274

[56] References Cited

U.S. PATENT DOCUMENTS 3,409,640 11/1968 Villani ..................... 260/370.8
4,127,717 11/1978 Hauck et al. ............. 544/154
4,136,116 1/1979 Kyburz et al. ........... 260/501.1 X

FOREIGN PATENT DOCUMENTS 1017696 1/1966 United Kingdom .

OTHER PUBLICATIONS

C.A., Hauck et al., 90: 121299w (1979).
Remers, et al.; J. Med. Chem., 14, (1971), pp. 331–335.
C.A., Sandoz, 59: 7495d (1963).
C.A., Merck, 63: 1758d (1965).
C.A., Villani, 70: 68009k (1969).
C.A., Russel, 71: 124063h (1969).
C.A. Kyburg et al., 72: 55104d (1970).
C.A., Russel, 72: 100376g (1970).
C.A., Russel, 72: 100377h (1970).
C.A., Russel, 72: 100379k (1970).
C.A., Russel, 72: 111170m (1970).
C.A., Russel, 72: 132395d (1970).
C.A., Davis, 76: 112871k (1972).
C.A., Kyburg, et al., 83: 192949z (1975).
Dostert, et al.; Helv. Chim. Acta., 53 (1970), pp. 882–897; 897–904.
C.A., Lippmann et al, 72: 1938k (1970).

Primary Examiner—Joseph Paul Brust
Attorney, Agent, or Firm—Jon S. Saxe; Bernard S. Leon; Matthew Boxer

[57] ABSTRACT

1-[2-(4,5,10,11-Tetrahydro-1H-dibenzo[a,d]cyclohept-en-5-yl)ethyl]pyrrolidine of the formula

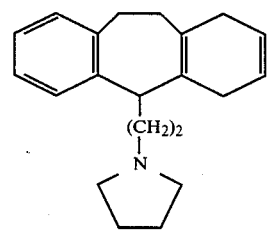

and its pharmaceutically acceptable acid addition salts, prepared through various intermediates, are described. The compounds have valuable histamine-$H_1$ antagonistic properties and are suitable for the control or prevention of allergic reactions, such as, urticaria, hay fever, anaphylaxis and over-sensitivity to medicaments.

2 Claims, No Drawings

CYCLOHEPTENE DERIVATIVES

BRIEF SUMMARY OF THE INVENTION

The invention relates to 1-[2-(4,5,10,11-tetrahydro-1H-dibenzo[a,d]cyclohepten-5-yl)ethyl]pyrrolidine of the formula

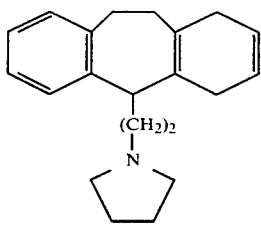

and its pharmaceutically acceptable acid addition salts, which have valuable histamine-$H_1$ antagonistic properties and are suitable for the control or prevention of allergic reactions such as urticaria, hay fever, anaphylaxis and over-sensitivity to medicaments.

In another aspect the invention relates to the intermediate 1,4,10,11-tetrahydro-5H-dibenzo[a,d]cycloheptene.

In still another aspect the invention relates to the intermediates of the formula

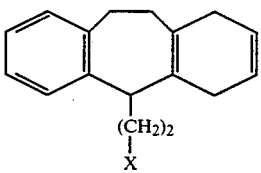

wherein X is a leaving group.

DETAILED DESCRIPTION OF THE INVENTION

The invention relates to cycloheptene derivatives. In particular, it relates to 1-[2-(4,5,10,11-tetrahydro-1H-dibenzo[a,d]cyclohepten-5-yl)-ethyl]pyrrolidine of the formula

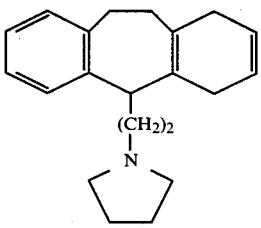

or a pharmaceutically acceptable acid addition salt thereof.

The compound possesses valuable therapeutic properties and can be used in the control or prevention of illnesses. Objects of the invention are the compound of formula I and its pharmaceutically acceptable acid addition salts per se or as pharmaceutically active substances, a process for their preparation, intermediates used in said process, medicaments containing the compound of formula I or a pharmaceutically acceptable acid addition salt thereof.

As used herein, the term "leaving group" includes halogen atoms, such as, chlorine, bromine and iodine; sulfonic acid groups, such as, methanesulfonyloxy, p-toluenesulfonyloxy, p-bromobenzenesulfonyloxy, benzenesulfonyloxy and the like; and other equivalent leaving groups. The term "alkyl" denotes a lower alkyl group of 1 to 7 carbon atoms, for example, methyl, ethyl, propyl, pentyl, heptyl and the like. The term "aryl" denotes an aromatic hydrocarbon radical, for example, phenyl, naphthyl and the like.

The term "pharmaceutically acceptable acid addition salt" includes pharmaceutically acceptable salts of the compound of formula I not only with inorganic acids, such as, hydrochloric acid, hydrobromic acid, phosphoric acid, sulfuric acid and the like, but also with organic acids, such as, maleic acid, citric acid, acetic acid, succinic acid, malic acid, tartaric acid, camphorsulfonic acid, mandelic acid, fumaric acid, methanesulfonic acid, p-toluenesulfonic acid and the like. The preparations of the pharmaceutically acceptable acid addition salts is carried out according to known methods familiar to any person of ordinary skill in the art.

The compound of formula I contains an asymmetric carbon atom. Therefore, the invention includes not only the optically active forms but also mixtures thereof, especially, the racemate. The resolution of the racemate can be carried out according to known methods, for example, by fractional crystallization of an acid addition salt of the compounds of formula I with an optically active acid, for example, with tartaric acid, camphorsulfonic acid, mandelic acid and the like. The optically active forms can, however, also be obtained by using an optically active starting material in process variant (c) described hereinafter.

A preferred pharmaceutically acceptable acid addition salt of the compound of formula I is 1-[2-(4,5,10,11-tetrahydro-1H-dibenzo[a,d]cyclohepten-5-yl)ethyl]pyrrolidine maleate.

The compound of formula I, that is, 1-[2-(4,5,10,11-tetrahydro-1H-dibenzo[a,d]cyclohepten-5-yl)ethyl]pyrrolidine, and its pharmaceutically acceptable acid addition salts can be prepared by (a) appropriately reducing 1-[2-(10,11-dihydro-5H-dibenzo[a,d]cyclohepten-5-yl)ethyl]pyrrolidine, or (b) reacting 1,4,10,11-tetrahydro-5H-dibenzo[a,d]cycloheptene in the presence of a strong base with a compound of the formula

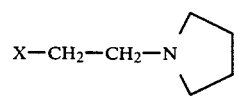

wherein X is a leaving group, or (c) reacting a compound of the formula

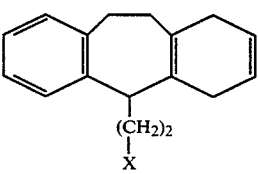

wherein X is as previously described, with pyrrolidine, and (d) isolating the resulting 1-[2-(4,5,10,11-tetrahydro-1H-dibenzo[a,d]cyclohepten-5-yl)ethyl]pyrrolidine as the free base or as a pharmaceutically acceptable acid addition salt.

According to process variant (a) of the invention, the compound of formula I can be prepared by 1,4-reducing one of the two aromatic rings in 1-[2-(10,11-dihydro-5H-dibenzo[a,b]cyclohepten-5-yl)ethyl]pyrrolidine. As the reducing agent there can be used, for example, an alkali metal such as lithium, sodium or potassium, in which case the solvent used is liquid ammonia or an amine which is suitable for such reductions, for example, methylamine, ethylamine, dimethylamine or the like. Conveniently, this 1,4-reduction is carried out in the presence of a proton donor and a solubilizer. Preferred proton donors are alcohols, such as, methanol, ethanol, propanol, isopropanol, butanol, t-butanol, 1,1-dimethylpropanol, ethyleneglycol monomethyl ether, propyleneglycol monomethyl ether and the like. Suitable solubilizers are, for example, ethers such as diethyl ether, t-butyl methyl ether, tetrahydrofuran, dioxane, ethyleneglycol dimethyl ether, diglyme and the like. The temperature at which this 1,4-reduction is carried out depends on the solvent used and lies in a range of about $-50°$ C. to the boiling point of the reaction mixture.

The 1,4-reduction can be carried out, for example, by pre-preparing a solution of 1-[2-(10,11-dihydro-5H-dibenzo[a,d]cyclohepten-5-yl)ethyl]pyrrolidine in a mixture of the solvent, preferably boiling ammonia, the solubilizer, preferably dry tetrahydrofuran, and the proton donor, preferably dry t-butanol or ethanol, and treating this solution with the alkali metal, preferably lithium or sodium.

The 1,4-reduction can, however, also be carried out readily in the opposite manner, that is, a solution of the alkali metal in the solvent can be prepared and this solution can be treated with a solution of 1-[2-(10,11-dihydro-5H-dibenzo[a,d]cyclohepten-5-yl)ethyl]pyrrolidine in a mixture of solubilizer and proton donor.

A further embodiment comprises adding the proton donor to the reaction mixture only after the 1,4-reduction has been completed. In this case, acidic ammonium salts such as ammonium chloride and the like are also suitable as proton donors.

Finally, the desired 1,4-reduction can also be carried out electrochemically. The electrochemical 1,4-reduction can be carried out in an undivided cell or in a divided cell. An undivided cell is preferred. The cathode material is not critical and, accordingly, platinum, graphite, mercury, lead, nickel, aluminum and the like, can be used. Platinum is preferably used as the cathode material. Platinum is the preferred anode material, although lead or graphite or another non-corroding material can also be used. As solvents there can be used amines, such as, methylamine, propylamine and ethylenediamine, or the like. If necessary, solubilizers, such as, tetrahydrofuran and diethyleneglycol dimethyl ether, and/or proton donors, such as, ethanol and t-butanol can also be used. Suitable conducting salts for this process aspect are, for example, lithium chloride, sodium chloride, tetrabutylammonium chloride and the like. The temperature at which this 1,4-reduction is carried out is not critical and it can accordingly be carried out at a temperature range of about $-20°$ C. to about 100° C., depending on the solvent used.

In an especially preferred embodiment, methylamine is used as the solvent, lithium chloride is used as the conducting salt and platinum is used as the anode and cathode material and the 1,4-reduction is carried out at a temperature of about $-10°$ C.

According to process variant (b) of the invention, the compound of formula I can be prepared by reacting 1,4,10,11-tetrahydro-5H-dibenzo[a,d]cycloheptene in the presence of a strong base with a compound of formula II. Conveniently, the 1,4,10,11-tetrahydro-5H-dibenzo[a,d]cycloheptene in an inert organic solvent, for example, in an ether, such as, tetrahydrofuran, dioxane, diethyl ether, dimethoxyethane, diglyme, t-butyl methyl ether or the like, or in a mixture thereof with alkanes, such as, for example, pentane, hexane and heptane, is converted with a strong base, for example, with an alkyl lithium or aryl lithium compound, such as, n-butyl lithium, methyl lithium and phenyl lithium or with an alkali metal amide, such as, lithium diisopropylamide and sodium amide, or with sodium hydride or the like, into the corresponding anion. The resulting compound is reacted with a compound of formula II. Depending on the base used the reaction can be carried out at a temperature of about $-70°$ C. to about room temperature.

According to process variant (c) of the invention, the compound of formula I can be prepared by reacting a compound of formula III with pyrrolidine. This reaction is conveniently carried out in an inert organic solvent in the presence of an acid-binding agent. Suitable solvents for this process aspect comprise, for example, ethers such as diethyl ether, t-butyl methyl ether, tetrahydrofuran, ethyleneglycol dimethyl ether and the like; alcohols such as ethanol, ethyleneglycol and the like; and excess pyrrolidine. As acid-binding agents there can be used inorganic bases, such as, potassium and sodium carbonate and the like, or organic bases such as triethylamine, quinuclidine and the like, or excess pyrrolidine. In a preferred embodiment, excess pyrrolidine is used as the solvent and simultaneously as the acid-binding agent. The temperature at which the reaction is carried out can vary in a range from about 0° C. to the boiling point of the reaction mixture and depends, of course, on the reactivity of the leaving group denoted by X.

In accordance with the invention, the compound of formula I is isolated as the free base or as a pharmaceutically acceptable acid addition salt. The isolation of the free base or a pharmaceutically acceptable acid addition salt thereof is carried out according to known methods familiar to any person of ordinary skill in the art; for example, by extraction or filtration techniques, by optional fractional crystallization, by chromatographic methods, such as, gas chromatography and high pressure-liquid chromatography, by distillation or by suitable combination of several of these known methods.

The 1-[2-(10,11-dihydro-5H-dibenzo[a,d]cyclohepten-5-yl)ethyl]pyrrolidine used as the starting material in process variant (a) is a known substance. However, various Examples hereinafter contain detailed information concerning the preparation of this substance.

The 1,4,10,11-tetrahydro-5H-dibenzo[a,d]cycloheptene used as the starting material in process variant (b) is conveniently prepared from the known 10,11-dihydro-5-H-dibenzo[a,d]cycloheptene by appropriate reduction in analogy to process variant (a) described above.

The compounds of formula III used as starting materials in process variant (c) can be prepared by appropriately reducing 10,11-dihydro-5H-dibenzo[a,d]cycloheptene-5-ethanol in analogy to process variant (a) described above and converting the hydroxy group in the resulting 1,4,10,11-tetrahydro-5H-dibenzo[a,d]cycloheptene-5-ethanol into a leaving group. This conversion is carried out according to known methods and familiar to any person skilled in the art; for example, by treating 1,4,10,11-tetrahydro-5H-dibenzo[a,d]cycloheptene-5-ethanol with a halogenating agent, such as, thionyl chloride, phosphorus oxychloride, phosphorus pentachloride, carbon tetrabromide/triphenylphosphine, iodine/red phosphorus or the like, or with a reactive sulfonic acid derivative, such as, mesyl chloride, tosyl chloride, brosyl chloride, benzenesulfonic acid chloride or the like and, if desired, replacing the sulfonic acid ester by a halogen atom according to known methods. Although 10,11-dihydro-5H-dibenzo[a,d]cycloheptene-5-ethanol is a known substance, certain Examples hereinafter contain detailed information concerning the preparation of this substance.

The compounds of formula III and 1,4,10,11-tetrahydro-5H-dibenzo[a,d]cycloheptene also form part of the invention.

Surprisingly, it has been found that the compound of formula I and its pharmaceutically acceptable acid addition salts are capable of inhibiting the $H_1$-action of histamine. Accordingly, they are valuable histamine-$H_1$ antagonistic active substances and are suitable, in particular, for the control or prevention of allergic reactions, for example, urticaria, hay fever, anaphylaxis and oversensitivity to medicaments. These histamine-$H_1$ antagonistic properties can be determined as described hereinafter on male and female guinea pigs weighing 240 to 300 g (SPF, Füllinsdorf):

The feed is withdrawn from the experimental animals (10 per dosage) for 24 hours before the beginning of the experiment, although water is supplied ad libitum. One hour after oral administration of a solution of the test substance (10 ml/kg), the experimental animals receive a lethal dosage of histamine dihydrochloride (10 mg/kg s.c.). Unprotected animals, that is, animals treated only with histamine dihydrochloride, die within 1 hour. After counting the surviving protected animals, the $ED_{50}$ is that dosage which is required to protect from death 50% of the animals treated with the test substance.

1-[2-(4,5,10,11-Tetrahydro-1H-dibenzo[a,d]cyclohepten-5-yl)ethyl]pyrrolidine maleate was found to have an $ED_{50}$ of 0.18 mg/kg p.o. and an $LD_{50}$ of 200 mg/kg (after oral administration on 5 successive days to mice).

The compound of formula I and its pharmaceutically acceptable acid addition salts can be used as medicaments, for example, in the form of pharmaceutical preparations. The pharmaceutical preparations can be administered orally, for example, in the form of tablets, coated tablets, dragées, hard and soft gelatine capsules, solutions, emulsions or suspensions. The administration can, however, also be carried out rectally, for example, in the form of suppositories, or parenterally, for example, in the form of injectables.

For the preparation of pharmaceutical formulation, the compound of formula I or a pharmaceutically acceptable acid addition salt thereof can be processed with pharmaceutical inert, inorganic or organic carriers. Examples of carriers which can be used for tablets, coated tablets, dragées and hard gelatine cpasules comprise lactose, maize starch or derivatives thereof, talc, stearic acid or its salts and the like. Suitable carriers for soft gelatine capsules are, for example, vegetable oils, waxes, fats, semi-solid and liquid polyols and the like. Depending on the nature of the active substance, no carriers are, however, generally necessary in the case of soft gelatine capsules. Suitable carriers for the preparation of solutions and syrups are, for example, water, polyols, saccharose, invert sugar, glucose and the like. Suitable carriers for injection solutions are, for example, water, alcohols, polyols, glycerine, vegetable oils and the like. Suitable carriers for suppositories are, for example, natural or hardened oils, waxes, fats, semi-liquid or liquid polyols and the like.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

As mentioned earlier, medicaments or compositions containing the compound of formula I or a pharmaceutically acceptable acid addition salt thereof are also an object of the invention. A process for the preparation of such medicaments comprises bringing the compound of formula I or a pharmaceutically acceptable acid addition salt thereof and, if desired, one or more other therapeutically valuable substances into a galenical administration form. As mentioned earlier, the compound of formula I and its pharmaceutically acceptable acid addition salts can be used in the control or prevention of illnesses. In particular, they can be used in the control or prevention of allergic reactions such as urticaria, hay fever, anaphylaxis and over-sensitivity to medicaments. The dosage can vary within wide limits and is, of course, fitted to the individual requirements in each particular case. In general, in the case of oral administration a daily dosage of about 10 mg to 150 mg can be used.

The Examples which follow further illustrate the invention. All temperatures are given in degrees Centigrade.

EXAMPLE 1

Preparation of 1-[2-(4,5,10,11-tetrahydro-1H-dibenzo[a,d]cyclohepten-5-yl)ethyl]pyrrolidine (a) A mixture of 208 g of 10,11-dihydro-5H-dibenzo[a,d]cyclohepten-5-one, 2 l of ethanol, 200 g of sodium hydroxide and 300 g of zinc powder is heated to boiling under reflux while stirring for 2 hours. The still warm mixture is filtered over kieselguhr while backwashing with about 1 l of methanol. After concentration of the yellow solution to about 1 l, the thick paste obtained is partitioned between 2 l of chloroform and 1 l of water. The alkaline-aqueous phase is adjusted to pH 3 to 4 with about 400 ml of concentrated hydrochloric acid while cooling with ice and extracted with 1 l of chloroform. The combined chloroform extracts are washed with water until they are neutral and subsequently dried over magnesium sulfate in the presence of a small amount of active carbon. After filtration and concentration of the clear, light yellowish solution, there is obtained 10,11-dihydro-5H-dibenzo[a,d]cyclohepten-5-ol as an almost white, crystalline mass with a melting point of 89–91°.

By recrystallization of a sample of this material from ether/petroleum ether there is obtained pure product of melting point 92°–93° C.

(b) 350 ml of thionyl chloride are added dropwise at a temperature of 30 to 40° to a solution of 201.5 g of crude 10,11-dihydro-5H-dibenzo[a,d]cyclohepten-5-ol in 700 ml of dry benzene over a period of 40 minutes. Subsequently, the mixture is heated to boiling under reflux for an additional 1.5 hours and concentrated in vacuo. The residue is diluted 2 to 3 times with 300 ml of benzene each time and in each case again evaporated. There is obtained 5-chloro-10,11-dihydro-5H-dibenzo[a,d]cycloheptene as a beige crystalline mass of melting point 99–101° which is used in the next step without further purification. By recrystallization from carbon tetrachloride there is obtained material of melting point 104°–105° C.

(c) A mixture of 11.4 g of magnesium shavings, 151.5 g of diethyl malonate and 300 ml of dry ethanol is warmed to 60° under argon over a period of 30 minutes. After the vigorous reaction has faded, the mixture is heated to boiling under reflux for an additional 1 hour and then concentrated in vacuo. The residue is treated twice with 300 ml of dry benzene each time and in each case evaporated well. The residue obtained is dissolved under argon in 350 ml of dry tetrahydrofuran. Thereto there is added dropwise at room temperature over a period of 20 minutes a solution of 195.5 g of 5-chloro-10,11-dihydro-5H-dibenzo[a,d]cycloheptene in 500 ml of dry tetrahydrofuran. The mixture is heated to boiling under reflux overnight while stirring and then evaporated in vacuo. The residue obtained is partitioned between 2.0 l of toluene and 500 ml of ice-water. The organic phase is washed successively twice with 500 ml of 1N hydrochloric acid each time, twice with 500 ml of water each time, twice with 250 ml of saturated sodium bicarbonate solution each time and several times with water, dried over magnesium sulfate and evaporated in vacuo. Diethyl 10,11-dihydro-5H-dibenzo[a,d]cycloheptene-5-malonate is obtained as an orange oil.

(d) A solution of 305 g of crude diethyl 10,11-dihydro-5H-dibenzo[a,d]cycloheptene-5-malonate and 138 g of potassium hydroxide in 1.5 l of ethanol and 400 ml of water is heated to boiling under reflux for 1.5 hours while stirring and subsequently evaporated in vacuo. The residue obtained is partitioned between 1 l of ether and 1 l of ice-water. The aqueous, alkaline phase is extracted further with 500 ml of ether, made acid with about 220 ml of concentrated hydrochloric acid while cooling with ice and extracted with 2 l of ether. The ethereal phase is washed three times with 500 ml of water each time and the aqueous washings are back-extracted with 1 l of ether. The combined ether extracts are washed for an additional three to four times with saturated sodium chloride solution, dried over magnesium sulfate and concentrated to a volume of about 400 ml. After dilution with 300 ml of petroleum ether, the clear solution obtained is cooled in an ice-bath and left to stand at 4° overnight. The crystallized-out material is removed by filtration under suction while back-washing with petroleum ether and dried at 50° in a vacuum drying oven. There is obtained 10,11-dihydro-5H-dibenzo[a,d]cycloheptene-5-malonic acid of melting point 183° (with decarboxylation).

(e) 200 g of 10,11-dihydro-5H-dibenzo[a,d]cycloheptene-5-malonic acid are heated to 180° while stirring for 30 minutes. After cooling to 120°, the residue is treated with about 1 l of benzene and heated to boiling while stirring and under reflux until all crystallized-out material has again dissolved. Subsequently, the mixture is treated with 500 ml of hexane, cooled to about 10° while stirring and while cooling with ice, left to stand in the cold overnight and subsequently the crystal slurry obtained is removed by filtration under suction. After washing with petroleum ether and drying at 50° in a vacuum drying oven, there is obtained 10,11-dihydro-5H-dibenzo[a,d]cycloheptene-5-acetic acid as beige crystals of melting point 163°–165°.

(f) A mixture of 160 g of 10,11-dihydro-5H-dibenzo[a,d]cycloheptene-5-acetic acid and 230 ml of thionyl chloride is heated to boiling under reflux for 2.5 hours. After concentration of the mixture in vacuo, the residue is treated twice with 300 ml of dry benzene each time and in each case evaporated to dryness. 10,11-Dihydro-5H-dibenzo[a,d]cycloheptene-5-acetic acid chloride is obtained as a red-brown oil.

(g) A mixture of 270 ml of pyrrolidine and 400 ml of dry benzene is treated dropwise under an argon atmosphere at 0 to 20° over a period of 1 hour with a solution of 174.4 g of 10,11-dihydro-5H-dibenzo[a,d]cycloheptene-5-acetic acid chloride to 400 ml of dry benzene. The mixture is heated to boiling under reflux for an additional 1 hour, left to cool to about 30° and poured into about 2 l of ice-water. The aqueous phase is separated and extracted with 1 l of benzene. The combined organic extracts are washed successively twice with 500 ml of 2N sodium hydroxide each time, 500 ml of water, 500 ml of 2N hydrochloric acid and twice to three times with 500 ml of saturated sodium chloride solution each time, dried over magnesium sulfate and evaporated. After taking up the residue in 500 ml of hot acetone, the mixture is left to cool to about 50° and treated with 1.2 l of petroleum ether. The mixture is left to stand at 4° overnight and there is obtained, after removing by filtration the crystallized-out material, 1-[(10,11-dihydro-5H-dibenzo[a,d]cyclohepten-5-yl)acetyl]pyrrolidine of melting point 130°–131°. From the mother liquor there is obtained a second portion of the desired amide with a melting point of 128°–130°.

(h) A mixture of 28.5 g of lithium aluminum hydride and 300 ml of dry dioxane, stirred under argon, is treated dropwise over a period of 1.25 hours with a solution of 230 g of 1-[(10,11-dihydro-5H-dibenzo[a,d-]cyclohepten-5-yl)acetyl]-pyrrolidine in 700 ml of dry dioxane, whereby the mixture is heated to boiling under reflux. 10 minutes after completion of the addition, the mixture is cooled to about 10°–15° and excess lithium aluminum hydride is destroyed by the cautious addition of 200 ml of ethyl acetate, the temperature rising to about 40°. The mixture is subsequently cooled to about 10° and hydrolyzed by the slow dropwise addition of about 250 ml of water while cooling well. The mixture is suction filtered while back-washing with about 200 ml of chloroform and the filtrate is evaporated in vacuo. The residual brown oil is taken up in 1 l of ether and extracted successively with 300 ml of 2N hydrochloric acid, 150 ml of 2N hydrochloric acid and twice with 100 ml of water each time. The acid-aqueous phase is made basic with about 100 ml of 28 percent sodium hydroxide while cooling with ice and extracted successively with 500 ml of hexane and twice with 300 ml of hexane each time. The organic extracts are washed twice with 250 ml of saturated sodium chloride solution each time and twice with 250 ml of distilled water each time, dried over magnesium aluminum in the presence of a spatula tip of active carbon and evaporated in vacuo. After drying the residue at 40° in a high vacuum, there is obtained 1-[2-(10,11-dihydro-5H-dibenzo[a,d]cyclohepten-5-yl)ethyl]pyrrolidine as a light yellow oil which crystallizes slowly; m.p. 51°–53°. By distillation of the crude base under argon over a Hickmann head at 163°–165°/0.09 Torr there is obtained pure material of melting point 53.5°–54°.

(i) 10.4 g of lithium are added to a mixture of 2.6 l of dry ammonia and 1.6 l of dry tetrahydrofuran at −50° under an argon atmosphere. After 2.5 minutes, the deep blue solution is treated while stirring well at −50° to −43° over a period of 6 minutes with a solution, pre-cooled to −50°, of 150 g of 1-[2-(10,11-dihydro-5H-dibenzo[a,d]cyclohepten-5-yl)ethyl]pyrrolidine and 351 g of t-butanol in 1.8 l of dry tetrahydrofuran. After completion of the addition, the dark blue mixture is stirred at −43° to −39° until decolorization has occurred (about 10 minutes). After an additional 2 minutes, the mixture is treated with 12.0 g of sodium benzoate and subsequently the ammonia is removed. The residue is subsequently washed six times with 500 ml of saturated sodium chloride solution each time, dried over magnesium sulfate and evaporated in vacuo. The light brown oil obtained is purified by column chromatography on 500 g of aluminium oxide (activity grade II, neutral) using benzene for the elution, there being obtained crude 1-[2-(4,5,10,11-tetrahydro-1H-dibenzo[a,d]cyclohepten-5-yl)ethyl]pyrrolidine as a light yellow oil which crystallizes slowly upon standing.

(j) 660 g of crude 1-[2-(4,5,10,11-tetrahydro-1H-dibenzo[a,d]cyclohepten-5-yl)ethyl]pyrrolidine are dissolved in 3.0 l of acetone under an argon atmosphere while warming slightly (to about 40°). The solution obtained is cooled to about 10° and treated while stirring with a solution, pre-cooled to about 10°, of 264.0 g of maleic acid in 1.6 l of acetone and diluted with 4.0 l of n-hexane while passing argon through the mixture. After 15 hours at room temperature and with the exclusion of light, the resulting crystal slurry is filtered under suction, washed twice with 1.0 l of petroleum ether each time and dried at room temperature in a vacuum drying oven for 20 hours. There is obtained 1-[2-(4,5,10,11-tetrahydro-1H-dibenzo[a,d]cyclohepten-5-yl)ethyl]pyrrolidine maleate of melting point 127°–129°. By concentration of the mother liquor to about 1 l there is obtained a second portion of melting point 123°–125°.

(k) A mixture of 8 g of 1-[2-(4,5,10,11-tetrahydro-1H-dibenzo[a,d]cyclohepten-5-yl)ethyl]pyrrolidine maleate, 20 ml of 3N sodium hydroxide and 50 ml of ether is shaken until two clear phases result. After separation of the aqueous phase, the ethereal solution is dried over magnesium sulfate and evaporated. There is obtained crystalline 1-[2-(4,5,10,11-tetrahydro-1H-dibenzo[a,d]cyclohepten-5-yl)ethyl]pyrrolidine of melting point 57°–58.5°. The melting point rises to 61°–63° after recrystallization from low-boiling petroleum ether at −25°.

(l) By high pressure-liquid chromatography of 10 g of the above material on two commercially obtainable pre-packed silica gel columns (5.7 × 30 cm) connected in series there is obtained, after nine-fold recycling using 10% tetrahydrofuran and 0.5% isopropylamine in n-hexane for the elution and recrystallization from petroleum ether (low-boiling) at −25°, pure 1-[2-(4,5,10,11-tetrahydro-1H-dibenzo[a,d]cyclohepten-5-yl)ethyl]pyrrolidine of melting point 63°–65°.

After recrystallization from acetone/n-hexane, the maleic acid salt prepared from the above material has a melting point of 129°–131°.

EXAMPLE 2

Preparation of 1-[2-(4,5,10,11-tetrahydro-1H-dibenzo[a,d]cyclohepten-5-yl)ethyl]pyrrolidine (a) A mixture, stirred at −40°, of 1.28 l of dry tetrahydrofuran and 2.1 l of dry liquid ammonia is treated with 8.6 g of lithium wire. The mixture is stirred for 2 minutes and subsequently there is added thereto over a period of 6 minutes a solution, pre-cooled to −40°, of 80.0 g of 10,11-dihydro-5H-dibenzo[a,d]cycloheptene in 1.44 l of dry tetrahydrofuran and 280 g of t-butanol. After a color change from blue to colorless, the mixture is treated with 6.0 g of sodium benzoate and the ammonia is evaporated. The mixture is washed three times with 500 ml of water each time. The combined aqueous washings are extracted twice with 1.0 l of ether each time. The organic phases are combined, washed with saturated sodium chloride solution, dried over magnesium sulfate and evaporated. The oily residue is purified by fractional crystallization from petroleum ether (low-boiling) at −25°. There is obtained 1,4,10,11-tetrahydro-5H-dibenzo[a,d]cycloheptene as white crystals of melting point 42.5°–43°.

(b) 1.0 g of 1,4,10,11-tetrahydro-5H-dibenzo[a,d]cycloheptene in 20 ml of dry tetrahydrofuran are treated dropwise at between −70° and −60° with 9.0 ml of an about 0.85M solution of n-butyl lithium in hexane. The mixture is stirred at −70° for 60 minutes and at −30° for 30 minutes, a solution of 2.1 g of 2-chloroethylpyrrolidine in 5 ml of dry tetrahydrofuran at −30° is added dropwise thereto and subsequently the mixture is stirred at −30° for an additional 30 minutes, at 0° to 5° for 3 hours and at room temperature for 30 minutes. After evaporation of the mixture, the residue remaining is dissolved in toluene and washed ion-free with water. The organic phase is filtered over aluminum oxide (activity grade II, neutral) using toluene for the elution. Crude 1-[2-(4,5,10,11-tetrahydro-1H-dibenzo[a,d]cyclohepten-5-yl)ethyl]pyrrolidine is obtained.

By preparative gas chromatography on a 2 m long (diameter: 40 mm) column loaded with 4% Carbowax 20M (polyethyleneglycol) [carrier material: Chromosorb G NAW (diatomaceous earth)] there is obtained at an oven temperature of 220° using helium as the carrier gas pure 1-[2-(4,5,10,11-tetrahydro-1H-dibenzo[a,d]cyclohepten-5-yl)ethyl]pyrrolidine of melting point 58°–60°.

EXAMPLE 3

Preparation of 1-[2-(4,5,10,11-tetrahydro-1H-dibenzo[a,d]cyclohepten-5-yl)ethyl]pyrrolidine (a) 1.0 g of 10,11-dihydro-5H-dibenzo[a,d]cycloheptene in 25 ml of dry tetrahydrofuran is treated dropwise at −70° with 6.8 ml of an about 1.14M solution of n-butyl lithium in hexane. The mixture is stirred at −70° for 60 minutes. There are subsequently added dropwise thereto at −30° 1.1 g of 2-chloroethylpyrrolidine in 2.5 ml of dry tetrahydrofuran and the mixture is stirred at −30° for 1 hour and at 0° to 5° for 3 hours. After evaporation of the mixture, the residue remaining is dissolved in toluene and washed with water. The organic phase is filtered over 10 g of aluminum oxide (activity grade II, neutral) using toluene for the elution. Crude 1-[2-(10,11-dihydro-5H-dibenzo[a,d]cyclohepten-5-yl)ethyl]pyrrolidine is obtained as a yellow oil.

After purification of this product in accordance with details in Example 1(h) there is obtained therefrom according to the details in Examples 1(i) to 1(l) pure 1-[2-(4,5,10,11-tetrahydro-1H-dibenzo[a,d]cyclohepten-5-yl)ethyl]pyrrolidine.

EXAMPLE 4

Preparation of
1-[2-(4,5,10,11-tetrahydro-1H-dibenzo[a,d]-cyclohepten-5-yl)ethyl]pyrrolidine (a) A solution of 58.3 g of dibenzosuberane in 750 ml of tetrahydrofuran, stirred under argon, is cooled to about 10° in an ice-bath and treated dropwise with 190 ml of an about 2M solution of butyl lithium in hexane. The dark red solution is heated to boiling under reflux for 2 hours. Ethylene oxide is conducted for 15 minutes into the solution, cooled to about 10°, subsequently the mixture is stirred at room temperature for 1 hour and finally heated to boiling under reflux for an additional 30 minutes. The cooled mixture is poured into 300 ml of ice-cold 3N hydrochloric acid and extracted twice with 2 l of ether each time. The organic extracts are washed with 500 ml of 2N potassium bicarbonate solution, combined, dried over magnesium sulfate and evaporated. The residue is boiled up three times with 50 ml of pentane each time. There is obtained 10,11-dihydro-5H-dibenzo[a,d]cycloheptene-5-ethanol in the form of a very viscous, yellowish oil, Rf: 0.25 (toluene/ethyl acetate, 9:1).

(b) A mixture of 80.0 g of 10,11-dihydro-5H-dibenzo[a,d]cycloheptene-5-ethanol, 195.7 ml of dry ethanol, 2.0 l of dry tetrahydrofuran and 3.2 l of dry distilled ammonia, stirred under argon, is treated at −30° to −31° with 25.09 g of sodium (3 to 4 pieces). After the exothermic reaction has faded, the mixture is stirred for about an additional 10 minutes and subsequently treated portionwise with a total of 60 g of ammonium chloride. After removal of the ammonia, the suspension remaining is washed three times with 800 ml of saturated ammonium chloride solution each time. The aqueous extracts are extracted twice with 1.5 l of ether each time. The organic phases are washed with 800 ml of water, combined, dried and evaporated in vacuo. There is obtained crude 4,5,10,11-tetrahydro-1H-dibenzo[a,d]cycloheptene-5-ethanol in the form of an oil which is used in the next step without further purification.

(c) A solution of 664 g of sodium hydroxide in 996 ml of water is added to a solution, stirred at room temperature, of 87.5 g of crude 4,5,10,11-tetrahydro-1H-dibenzo[a,d]cycloheptene-5-ethanol, 103.7 g of p-toluenesulfochloride and 7.2 g of benzyltriethylammonium chloride in 1440 ml of methylene chloride and the mixture is stirred at room temperature overnight. The mixture is treated with 2 l of ice-water and extracted with 3 l of methylene chloride. The organic extracts are washed neutral with water. The aqueous extracts remaining are subsequently back-extracted three times with 2 l of methylene chloride each time. The organic extracts are combined, dried over magnesium sulfate and evaporated. After four-fold recrystallization of the solid residue from toluene, there is obtained pure 2-[(4,5,10,11-tetrahydro-1H-dibenzo[a,d]cyclohepten-5-yl)ethyl]-p-toluenesulfonate of melting point 150°–151°.

(d) A suspension of 59.8 g of 2-(4,5,10,11)-tetrahydro-1H-dibenzo[a,d]cyclohepten-5-yl)ethyl-p-toluenesulfonate in 180 ml of pyrrolidine is stirred under argon at room temperature for 21 hours, subsequently poured into a mixture of ice and 300 ml of water and extracted twice with 1.2 l of distilled ether each time. The organic extracts are washed twice with 400 ml of water each time and a small amount of ice, combined, dried over magnesium sulfate and evaporated. The residue is taken up twice in 100 ml of dry toluene each time and the solutions obtained are in each case evaporated to dryness. There is obtained 1-[2-(4,5,10,11-tetrahydro-1H-dibenzo[a,d]cyclohepten-5-yl)ethyl]pyrrolidine in the form of an oil which crystallizes upon standing; m.p. 56°–57°. By recrystallization from pentane there is obtained product of melting point 62°.

(e) In analogy to the details in Example 1(j) there is obtained 1-[2-(4,5,10,11-tetrahydro-1H-dibenzo[(a,d]cyclohepten-5-yl)ethyl]pyrrolidine maleate of melting point 129°–130°.

EXAMPLE 5

Preparation of
1-[2-(4,5,10,11-tetrahydro-1H-dibenzo[a,d]cyclohepten-5-yl)ethyl]pyrrolidine (a) A solution of 237 g of 10,11-dihydro-5H-dibenzo[a,d]cycloheptene-5-acetic acid in 1 l of dry tetrahydrofuran is added dropwise over a period of 90 minutes to a suspension of 35.6 g of lithium aluminum hydride in 1.5 l of dry tetrahydrofuran stirred at 0° under argon. The mixture is subsequently heated to boiling under reflux for 90 minutes, cooled and successively treated dropwise with 35.6 ml of water, 35.6 ml of 15 percent sodium hydroxide and 106.8 ml of water. The resulting suspension is filtered with repeated back-washing with 2 l of tetrahydrofuran. After removal of the solvent in vacuo, the residue is taken up three times in 500 ml of toluene each time, the solutions obtained being in each case again evaporated. There is obtained pure 10,11-dihydro-5H-dibenzo[a,d]cycloheptene-5-ethanol in the form of an oil, which crystallizes slowly.

(b) The material obtained according to the preceding paragraph is converted into 1-[2-(4,5,10,11-tetrahydro-1H-dibenzo[a,d]cyclohepten-5-yl)ethyl]pyrrolidine in analogy to the details in Examples 4(b) to 4(f).

EXAMPLE 6

Preparation of
1-[2-(4,5,10,11-tetrahydro-1H-dibenzo[a,d]cyclohepten-5-yl)ethyl]pyrrolidine (a) A solution of 208.2 g of dibenzosuberone in 600 ml of dry ethanol is added dropwise over a period of 60 minutes to a solution of 39 g of sodium in 850 ml of dry ethanol cooled to 10° and stirred under argon. The mixture is stirred for 60 minutes at a temperature of 10° and subsequently treated over a period of 5 minutes with 318 g of triethylphosphonoacetate in 400 ml of ethanol (Horner reagent). Subsequently, the mixture is evaporated, and the residue is poured into a mixture of ice and 500 ml of water. After three-fold extraction with 1 l of hexane each time, the organic extracts are washed with 500 ml of water, combined, dried over magnesium sulfate and evaporated. The crude product obtained is recrystallized from 250 ml of petroleum ether (low-boiling), there being obtained crystalline ethyl 10,11-dihydro-5-dibenzo[a,d]cyclohepten-5-ylidene-acetate of melting point 54°.

(b) A solution of 516.8 g of ethyl 10,11-dihydro-5-dibenzo[a,d]cyclohepten-5-ylidene-acetate in 1.5 l of ethanol is hydrogenated while stirring over 51.7 g of 5 percent palladium/carbon for 48 hours at room temperature and normal pressure. After filtration and concentration of the mixture, there is obtained ethyl 10,11-dihydro-5H-dibenzo[a,d]cycloheptene-5-acetate in the form of an oil which is used in the next step without further purification.

(c) 513.2 g of ethyl 10,11-dihydro-5H-dibenzo[a,d]cycloheptene-5-acetate are treated with a solution of 130 g of potassium hydroxide in 900 ml of ethanol and 300 ml of water. The mixture is heated to boiling under reflux for 5.5 hours, poured into a mixture of ice and 1.5 l of water and extracted once with ether. The organic phase is back-extracted once with 500 ml of water. The aqueous phases are combined, made acid with 300 ml of 50 percent sulfuric acid and extracted twice with 3 l of ether each time. The ethereal extracts are washed with 1 l of water, combined, dried over magnesium sulfate and evaporated. The crude product yields, after recrystallization from tetrahydrofuran/hexane, 10,11-dihydro-5H-dibenzo[a,d]cycloheptene-5-acetic acid of melting point 163°–165°.

By concentration of the mother liquor in vacuo there is obtained a second portion of product of melting point 163°–165°.

(d) A solution of 446.4 g of 10,11-dihydro-5H-dibenzo[a,d]cycloheptene-5-acetic acid in 2.2 l of tetrahydrofuran, stirred under argon and cooled with ice-water, is treated portionwise with 87.0 g of sodium borohydride. The mixture is stirred for 30 minutes and subsequently a solution of 290 ml of freshly distilled boron trifluoride etherate in 300 ml of dry tetrahydrofuran is added dropwise thereto over a period of 90 minutes at a temperature of 10°. The mixture is stirred at 0° for 1 hour and at room temperature for 16 hours, cooled to 0° and treated dropwise over a period of 30 minutes with 400 ml of methanol. The mixture is stirred further at 0° for 15 minutes and at room temperature for 15 minutes and the solution is subsequently evaporated in vacuo. The residue is poured into a mixture of ice and 1 l of water, extracted three times with 2 l of ether each time and the organic extracts are washed successively with 1 l of 1.5N hydrochloric acid, with 1 l of 1.5N potassium bicarbonate solution and with 1 l of water. The organic phases are combined, dried over magnesium sulfate and evaporated. There is obtained 10,11-dihydro-5H-dibenzo[a,d]cycloheptene-5-ethanol in the form of an oil which crystallizes slowly upon standing.

(e) The material obtained according to the preceding paragraph is converted into 1-[2-(4,5,10,11-tetrahydro-1H-dibenzo[a,d]cyclohepten-5-yl)ethyl]pyrrolidine in analogy to the details in Examples 4(b) to 4(f).

EXAMPLE 7

Preparation of 1-[2-(4,5,10,11-tetrahydro-1H-dibenzo[a,d]cyclohepten-5-yl)ethyl]pyrrolidine (a) 1120 ml of a 20 percent (v/v) solution of diisobutylaluminum hydride in toluene are added dropwise over a period of 1 hour while cooling to a solution of 160.36 g of ethyl 10,11-dihydro-5H-dibenzo[a,d]cycloheptene-5-acetate in 1 l of dry toluene, cooled in ice-water and stirred under argon. The solution is subsequently stirred at room temperature for 16.5 hours, cautiously treated while cooling with 20 ml of dry methanol, stirred for an additional 30 minutes and finally acidified with 1.5 l of 3N hydrochloric acid while cooling well. The organic phase is separated and washed with 1 l of water and the acidic-aqueous phase is back-extracted twice more with 2 l of ether each time. After washing the ethereal extracts with 1 l of water, the organic phases are combined, dried over magnesium sulfate and evaporated. The residue is taken up twice in 200 ml of dry toluene each time, the solutions obtained being in each case again evaporated to dryness. There is obtained 10,11-dihydro-5H-dibenzo[a,d]cycloheptene-5-ethanol in the form of an oil which crystallizes only slowly upon standing.

(b) The material obtained according to the preceding paragraph is converted into 1-[2-(4,5,10,11-tetrahydro-1H-dibenzo[a,d]cyclohepten-5-yl)ethyl]pyrrolidine in analogy to the details in Examples 4(b) to 4(f).

EXAMPLE 8

Preparation of 1-[2-(4,5,10,11-tetrahydro-1H-dibenzo[a,d]cyclohepten-5-yl)ethyl]pyrrolidine 2.0 g of 1-[2-(10,11-dihydro-5H-dibenzo[a,d]cyclohepten-5-yl)ethyl]pyrrolidine and 2.5 g of lithium chloride are placed in a 100 ml glass vessel having a removable cover with 5 ground openings and fitted with a dry-ice condenser, thermometer, platinum sheet anode and cathode (each 2.5×2.5 cm, distance 2 cm). Subsequently, nitrogen is conducted through the apparatus for 20 minutes, the receiver is placed in a dry-ice/alcohol bath, the dry-ice condenser is charged with dry-ice and 70 g of methylamine are distilled directly into the apparatus from a pressure flask while stirring with a magnetic stirrer. Subsequently, a current of 2 amperes is applied, whereupon a voltage of 44 volts occurs and the cathode immediately becomes deep blue in color. The temperature is held at −10°. After a throughput of an amount of current of 3000 amperes (corresponding to 230% of the theoretical amount of current required for the complete conversion), the current is turned off and the solution is evaporated at 50° and under a slight vacuum. The residue is digested in hexane for a few minutes in an ultrasound bath. After filtration and evaporation, there is obtained crude 1-[2-(4,5,10,11-tetrahydro-1H-dibenzo[a,d]cyclohepten-5-yl)ethyl]pyrrolidine which is purified in analogy to the details in Examples 1(j) to 1(l).

EXAMPLE A

1-[2-4,5,10,11-Tetrahydro-1H-dibenzo[a,d]cyclohepten-5-yl)ethyl)pyrrolidine maleate can be used as follows as the active substance for the production of pharmaceutical preparations:

| Capsules | mg/capsule |
|---|---|
| Active substance | 6.98 |
| Maize starch | 20.00 |
| Lactose (powdered) | 40.00 |
| Lactose (crystalline) | 68.02 |
| Talc | 4.50 |
| Magnesium stearate | 0.50 |
| Capsule fill weight | 140.00 |

The active substance is mixed with the adjuvants and the mixture is sieved. After renewed mixing, the capsule fill mass obtained is filled into interlocking gelatine capsules of suitable size on a fully automatic capsule filling machine.

We claim:

1. A method of controlling or preventing allergic reactions which comprises administering to a host requiring such treatment an effective amount of 1-[2-(4,5,10,11-tetrahydro-1H-dibenzo[a,d]cyclohepten-5-yl)ethyl]pyrrolidine or a pharmaceutically acceptable acid addition salt thereof.

2. A method in accordance with claim 1, wherein 1-[2-(4,5,10,11-tetrahydro-1H-dibenzo[a,d]cyclohepten-5-yl)ethyl]pyrrolidine or a pharmaceutically acceptable acid addition salt thereof is administered orally in a daily dosage of about 10 mg to 150 mg.

* * * * *